(12) United States Patent
Ikuta

(10) Patent No.: US 6,461,420 B2
(45) Date of Patent: Oct. 8, 2002

(54) DENTAL ROOT CANAL FILLING MATERIAL

(75) Inventor: Tonami Ikuta, Kawaura-machi (JP)

(73) Assignee: GC Corporation, Tokyo (JP)

( * ) Notice: Subject to any disclaimer, the term of this patent is extended or adjusted under 35 U.S.C. 154(b) by 1 day.

(21) Appl. No.: 09/726,532

(22) Filed: Dec. 1, 2000

(65) Prior Publication Data

US 2001/0009131 A1 Jul. 26, 2001

(30) Foreign Application Priority Data

Dec. 8, 1999 (JP) .......................................... 11-348553

(51) Int. Cl.$^7$ .................................................. C09K 3/00
(52) U.S. Cl. ....................................................... 106/35
(58) Field of Search ........................................... 106/35

*Primary Examiner*—Elizabeth D. Wood
(74) *Attorney, Agent, or Firm*—Oblon, Spivak, McClelland, Maier & Neustadt, P.C.

(57) ABSTRACT

A dental root canal filling material that is a dental canal filling material used in a root canal filling method in an obturation method is disclosed, which contains 3 to 8% by weight of bone wax and has a softening temperature of 40° to 70° C., the dental root canal filling material being low in hardness and superior in fluidity with respect to its softened materials, and having a operability suitable in the root canal filling operation in the obturation method.

10 Claims, No Drawings

DENTAL ROOT CANAL FILLING MATERIAL

BACKGROUND OF THE INVENTION

1. Field of the Invention

The present invention relates to a dental root canal filling material that is heated for softening and filled in a root canal in the dental root canal treatment, and particularly, to a dental root canal filling material suitable for a root canal filling method in an obturation method.

2. Description of the Conventional Art

In general, as the therapy of dental pulp disease or apical periodontitis, there is carried out a root canal treatment in which, after pulpectomy, enlargement of root canal or root canal preparation is carried out, and a dental root canal filling material that is materially stable and is a stable substance to living bodies is filled in the obtained root canal, thereby keeping a root of the tooth harmless to a periodontal tissue. As this dental root canal filling material, those composed mainly of a gutta-percha and/or a balata, each of which is a natural resin, are generally used.

And, as a method for filling this dental root canal filling material in a root canal, are employed the following two modes:

(1) A lateral condensation method using a thin needle-like dental root canal filling material called a gutta-percha point; and (2) An obturation method for softening a dental root canal filling material having a low softening temperature and filling it.

The lateral condensation method is a filling method using the gutta-percha point formed into a thin needle-like shape having a different thickness, which is composed mainly of gutta-percha and/or a balata and contains zinc oxide, calcium carbonate, beeswax, a wax, a resin, etc. In this lateral condensation method, first of all, a gutta-percha point called a main point, having the same size as in a reamer and a file to be used during the root canal preparation, is filled, and then, several thinner gutta-percha points called an accessory point are filled under pressure in a gap between the main point and the root canal wall.

However, in order to completely seal the root canal according to this method, a skill and a time period are required to a considerable degree. Further, in the case where the root canal is curved or branched, it is difficult to complete the filling to an apical portion.

On the other hand, the obturation method is a method in which a dental root canal filling material generally comprising a gutta-percha and/or a balata and a paraffin wax as basic components, whose heat softening temperature is lowered to about 40° to 70° C. by compounding an appropriate combination of zinc oxide, white Japan wax, beeswax, barium sulfate, titanium oxide, resins, etc. therewith, is heated for softening and filled. Since this dental root canal filling material is softened at a relatively low temperature to obtain fluidity, it can be poured and filled in the root canal by using a syringe, etc. Accordingly, this method has rapidly developed as a method in which the filling can be effected without influences by the root canal shape. The reason why the dental root canal filling material is regulated to have a heat softening temperature of about 40° to 70° C. is as follows. That is, when the heat softening temperature is lower than 40° C., the setting becomes slow because that temperature is close to the oral cavity temperature, whereas when it exceeds 70° C., a burn possibly occurs.

However, since in the dental root canal filling material that are currently used for this method, their softened materials are relatively hard and low in heat reserve properties, it cannot be said that the fluidity to the filling into the details such as an apical portion is sufficient. Further, inconveniences are likely generated such that the setting starts during the filling works, whereby the filling becomes incomplete, and that the root canal sealing property is inferior.

SUMMARY OF THE INVENTION

The present invention is aimed to provide a dental root canal filling material capable of overcoming the defects of the conventional dental root canal filling material are used in the current obturation method as described above, which is low in hardness and superior in fluidity with respect to its softened materials, and which has a performance suitable in the root canal filling operation in the obturation method with high heat reserve properties.

Under such a circumstance, the present inventor made extensive and intensive investigations with respect to components that, when compounded in even small amounts in a dental root canal filling material that is used in the current obturation method, can lower the hardness, increase the fluidity and improve the heat reverse properties in terms of its softened materials. As a result, it has been unexpectedly found that it is proper to compound bone wax therewith, leading to the development of a dental root canal filling material of the present invention.

Specifically, the dental root canal filling material according to the present invention is a dental root canal filling material to be used in a root canal filling method in an obturation method, which contains 3 to 8% by weight of bone wax and has a softening temperature of 40° to 70° C.

DETAILED DESCRIPTION OF THE PREFERRED EMBODIMENTS

As constitutional components of the dental root canal filling material, with which the bone wax is to be compounded, according to the present invention, those used in a known dental root canal filling material having a heat softening temperature of 40° to 70° C., that is used in the root canal filling method in an obturation method, can be used. In general, known dental root canal filling material that can be used in the present invention comprises a gutta-percha and/or a balata and a paraffin wax as basic components and is compounded with an appropriate combination of zinc oxide, white Japan wax, beeswax, barium sulfate, titanium oxide, resins, etc. as well as other components such as zinc sulfide, eugenol, magnesium carbonate, various disinfectants, bactericides, pigments, etc.

The bone wax as referred to herein is a wax basically constituted by iodoform, spermaceti, and sesame oil, and having a melting point of 45° C. or lower and a penetration index of 80 or more at 35° C. A typical compounding ratio is one comprising 40% by weight of iodoform, 30% by weight of spermaceti, and 30% by weight of sesame oil. In the case where such bone wax is combined with the known dental root canal filling material having a heat softening temperature of 40° to 70° C., that is used in the root canal filling method in an obturation method, there are effects for lowering the hardness and improving the fluidity as well as an effect for increasing the heat reserve properties, thereby prolonging the margin of time for filling operation, in terms of its softened material, without substantially lowering the heat softening temperature. Further, it is possible to easily fill root canals having even a complicated shape, such as a curved root canal and a branched root canal. Accordingly, the present invention can much improve the operability required in the root canal filling method in an obturation method.

A suitable amount of the bone wax that can be contained in the root canal filling material is 3 to 8% by weight. When the containing amount of the bone wax is less than 3% by weight, the effects of the bone wax are not exhibited sufficiently. On the other hand, when it exceeds 8% by weight, the softened material is too low in hardness and excessively high in fluidity, so that it is impossible to pressurize the composition sufficiently during the filling, whereby it is difficult to fill the composition into the narrow portions. Accordingly, the dental root canal filling material that is used in the root canal filling method in an obturation method, according to the present invention, is required to contain 3 to 8% by weight of bone wax and have a softening temperature of 40° to 70° C.

The dental root canal filling material according to the present invention will be described in detail with reference to the following Examples, but it is to be not construed that the invention is limited thereto.

EXAMPLE 1

| | |
|---|---|
| Gutta-percha: | 11% by weight |
| Paraffin wax (melting point: 54° C.): | 11% by weight |
| Zinc oxide: | 39% by weight |
| Barium sulfate: | 32% by weight |
| Beeswax: | 1% by weight |
| Bonewax (made by Lukens Medical Corp.): | 6% by weight |

The above-described components were respectively weighed and kneaded under heat in a pressure kneader to prepare a dental root canal filling material having a softening temperature of about 55° C. The obtained dental root canal filling material was heated for softening at 7° C. higher than the softening temperature and subjected to root canal filling into a mandibular first molar in the root canal filling method in an obturation method. As a result, the softened material was properly soft, superior in fluidity during the filling and sufficient in heat reserve properties. Further, the softness and fluidity of the softened material were kept during the filling operation, and hence, the property of filling operation was very good. Moreover, the filling state in the root canal was confirmed by X-ray opacity. As a result, the root canal filling material was filled into the narrow portions of the curved root canal, and good results of the root canal filling were confirmed.

EXAMPLE 2

| | |
|---|---|
| Gutta-percha: | 25% by weight |
| Paraffin wax (melting point: 46° C.): | 20% by weight |
| Zinc oxide: | 30% by weight |
| Barium sulfate: | 15% by weight |
| Beeswax: | 1% by weight |
| White Japan wax | 1% by weight |
| Eugenol oil | 5% by weight |
| Bonewax (made by Lukens Medical Corp.): | 3% by weight |

The above-described components were respectively weighed and kneaded under heat in a pressure kneader to prepare a dental root canal filling material having a softening temperature of about 45° C. The obtained dental root canal filling material was subjected to root canal filling into a mandibular first molar in the same manner as in Example 1. As a result, the softened material was properly soft, superior in fluidity during the filling and sufficient in heat reserve properties. Further, the softness and fluidity of the softened material were kept during the filling operation, and hence, the property of filling operation was very good. Moreover, the filling state in the root canal was confirmed by X-ray opacity. As a result, the root canal filling material was filled into the narrow portions of the curved root canal, and good results of the root canal filling were confirmed.

EXAMPLE 3

| | |
|---|---|
| Balata polymer: | 40% by weight |
| Paraffin wax (melting point: 58° C.): | 15% by weight |
| Zinc oxide: | 20% by weight |
| Barium sulfate: | 7% by weight |
| White Japan wax | 1% by weight |
| Titanium oxide | 10% by weight |
| Bone wax (made by Lukens Medical Corp.): | 7% by weight |

The above-described components were respectively weighed and kneaded under heat in a pressure kneader to prepare a dental root canal filling material having a softening temperature of about 60° C. The obtained dental root canal filling material was subjected to root canal filling into a mandibular first molar in the same manner as in Example 1. As a result, the softened material was properly soft, superior in fluidity during the filling and sufficient in heat reserve properties. Further, the softness and fluidity of the softened material were kept during the filling operation, and hence, the property of filling operation was very good. Moreover, the filling state in the root canal was confirmed by X-ray opacity. As a result, the root canal filling material was filled into the narrow portions of the curved root canal, and good results of the root canal filling were confirmed.

EXAMPLE 4

96% by weight of a commercially available dental root canal filling material for the root canal filling method in an obturation method with a trade name "Obturation Gutta" (made by Toyo Chemical Industries, Inc.) , 4% by weight of bone wax (made by Lukens Medical Corp.) as a dental root canal filling material of the above components was prepared in the same manner as in Example 1. The obtained dental root canal filling material was subjected to root canal filling into a mandibular first molar in the same manner as in Example 1. As a result, the softened material was properly soft, superior in fluidity during the filling and sufficient in heat reserve properties. Further, the softness and fluidity of the softened material were kept during the filling operation, and hence, the property of filling operation was very good. Moreover, the filling state in the root canal was confirmed by X-ray opacity. As a result, the root canal filling material was filled into the narrow portions of the curved root canal, and good results of the root canal filling were confirmed.

Comparative Example 1

| | |
|---|---|
| Gutta-percha: | 11% by weight |
| Paraffin wax (melting point: 54° C.): | 11% by weight |
| Zinc oxide: | 45% by weight |

| | |
|---|---|
| -continued | |
| Barium sulfate: | 32% by weight |
| Beeswax | 1% by weight |

The above-described components were respectively weighed and kneaded under heat in a pressure kneader to prepare a dental root canal filling material having a softening temperature of about 57° C. The obtained dental root canal filling material was subjected to root canal filling into a mandibular first molar in the same manner as in Example 1. As a result, the softened material was slightly hard and somewhat insufficient in fluidity during the filling. Further, an increase in hardness of the softened material was confirmed during the filling operation. Moreover, the filling state in the root canal was confirmed by X-ray opacity. As a result, it was confirmed that the root canal filling material was not filled in a part of the narrow portions of the curved root canal.

Comparative Example 2

The commercially available dental root canal filling material for the root canal filling method in an obturation method with the trade name "Obturation Gutta" (made by Toyo Chemical Industries, Inc.) was subjected to root canal filling into a mandibular first molar in the same manner as in Example 1. As a result, the softened material was slightly hard and somewhat insufficient in fluidity during the filling. Further, an increase in hardness of the softened material was confirmed during the filling operation. Moreover, the filling state in the root canal was confirmed by X-ray opacity. As a result, it was confirmed that the root canal filling material was not filled in a part of the narrow portions of the curved root canal.

As described above in detail, the dental root canal filling material according to the present invention, when containing bone wax in a predetermined ratio with the known dental root canal filling material used in the root canal filling method in an obturation method, gives rise to effects for lowering the hardness and improving the fluidity as well as an effect for increasing the heat reserve properties, in terms of its softened material, without substantially lowering the heat softening temperature of the softened material. Further, it is possible to easily fill root canals having even a complicated shape, such as a curved root canal and a branched root canal. Accordingly, the present invention can much improve the operability required in the root canal filling method in an obturation method. Thus, the present invention is greatly valuable in contributing to the dental field.

While the invention has been described in detail and with reference to specific embodiments thereof, it will be apparent to one skilled in the art that various changes and modifications can be made therein without departing from the spirit and scope thereof.

What is claimed is:

1. A dental root canal filling material containing 3 to 8% by weight of bone wax, wherein said filling material has a softening temperature ranging from about 40 to 70° C.

2. The dental root canal filling material of claim 1, comprising 11% by weight of gutta-percha, 11% by weight of paraffin wax, 39% by weight of zinc oxide, 32% by weight of barium sulfate, 1% by weight of beeswax, and 6% by weight of bone wax.

3. The dental root canal filling material of claim 1, comprising 25% by weight of gutta-percha, 20% by weight of paraffin wax, 30% by weight of zinc oxide, 15% by weight of barium sulfate, 1% by weight of beeswax, 1% by weight of white Japan wax, 5% by weight of eugenol oil, and 3% by weight of bone wax.

4. The dental root canal filling material of claim 1, comprising 40% by weight of balata polymer, 15% by weight of paraffin wax, 20% by weight of zinc oxide, 7% by weight of barium sulfate, 1% by weight of white Japan wax, 10% by weight of Titanium oxide, and 7% by weight of Bone wax.

5. The dental root canal filling material of claim 1, further comprising one or more components selected from the group consisting of gutta-percha, balata and paraffin wax.

6. The dental root canal filling material of claim 5, further comprising one or more components selected from the group consisting of zinc oxide, white Japan wax, beeswax, barium sulfate, titanium oxide, and a resin.

7. The dental root canal filling material of claim 6, further comprising one or more components selected from the group consisting of zinc sulfide, magnesium carbonate, a disinfectant, a bactericide, and a pigment.

8. The dental root canal filling material of claim 1, wherein the bone wax comprises iodoform, spermaceti, and sesame oil.

9. The dental root canal filling material of claim 8, wherein the bone wax comprises 40% by weight of iodoform, 30% by weight of spermaceti, and 30% by weight of sesame oil.

10. The dental root canal filling material of claim 1, wherein said filling material has a softening temperature ranging from 40 to 70 ° C.

\* \* \* \* \*